US008182864B2

(12) United States Patent
Hahn et al.

(10) Patent No.: US 8,182,864 B2
(45) Date of Patent: May 22, 2012

(54) MODIFICATION METHOD OF MICROCHANNELS OF PDMS MICROCHIP USING SOL-GEL SOLUTION

(75) Inventors: Jong-Hoon Hahn, Pohang (KR); Jin Hee Park, Pohang (KR); Miok Shin, Seoul (KR)

(73) Assignees: Postech Academy-Industry Foundaction, Hyoja-Dong, Nam-Ku, Kyungsangbuk-Do, Pohang (KR); POSCO, Nam-Ku, Kyungsangbuk-Do, Pohang-Shi (KR)

( * ) Notice: Subject to any disclaimer, the term of this patent is extended or adjusted under 35 U.S.C. 154(b) by 607 days.

(21) Appl. No.: 12/190,764

(22) Filed: Aug. 13, 2008

(65) Prior Publication Data

US 2009/0117287 A1 May 7, 2009

Related U.S. Application Data

(60) Provisional application No. 60/955,815, filed on Aug. 14, 2007.

(51) Int. Cl.
*B05D 5/12* (2006.01)

(52) U.S. Cl. ...................... 427/97.7; 427/97.8; 427/98.3

(58) Field of Classification Search .................... 427/58, 427/97.7, 97.8, 98.3
See application file for complete search history.

(56) References Cited

U.S. PATENT DOCUMENTS

2007/0037411 A1* 2/2007 Balkenende et al. ......... 438/781

OTHER PUBLICATIONS

Papra et al., "Microfluidic Networks made of Poly(dimethylsiloxane), Si and Au-coated with Polyethylene Glycol for Patterning Proteins onto surfaces", Langmuir 2001, vol. 17, pp. 4090-4095.*

Efimenko, K. Wallace, W. E.; Genzer, J. Journal of Colloid and Interface Science 2002, 254, 306.

Ocvirk, G.; Munroe, M.; Tang, T.; Oleschuk, R.; Westra, K.; Harrison, D. J.Electrophoresis 2000, 21, 107.

Papra, A.; Bernard, A.; Juncker, D.; Larsen, N. B.; Michel, B.; Delamarche, E. Langmuir 2001, 17, 4090.

* cited by examiner

*Primary Examiner* — Brian K Talbot

(74) *Attorney, Agent, or Firm* — Lexyoume IP Group, PLLC

(57) ABSTRACT

The present invention provides a method for modification of microchannels of a polydimethylsiloxane (PDMS) microchip, which includes the steps of: a) mixing an alkoxysilane precursor, an alkyl alkoxysilane precursor, and a solvent to prepare a sol-gel solution; b) oxidizing microchannels of the PDMS microchip; and c) coating the oxidized microchannels with the sol-gel solution prepared in step a). The PDMS microchip modified according to the method of the present invention shows higher hydrophilicity than an unmodified PDMS microchip. And, when the modified PDMS channels are filled with an organic solvent, channel swelling can be reduced, and thus various organic solvents can be used for the modified PDMS microchip compared to an unmodified PDMS microchip. Further, it can be widely applied for various fields because absorptivity of non-polar substances can be reduced.

14 Claims, 12 Drawing Sheets
(8 of 12 Drawing Sheet(s) Filed in Color)

Pt wire glass

1. Corona discharge in defined microchannel

2. Filling of the sol-gel solution in microchannel
Reaction for 10 min, RT.

3. Removing of the remained sol-gel solution with acetonitrile and air push

4. Drying at -20 °C for 1 day and at 65 °C for 2 hours.

MODIFICATION METHOD OF MICROCHANNELS OF PDMS MICROCHIP USING SOL-GEL SOLUTION

CROSS REFERENCE TO RELATED APPLICATION

The present application claims priority to and the benefit of U.S. provisional application No. 60/955,815 filed in the United State Patent and Trademark Office on Aug. 14, 2007, the entire content of which is incorporated hereinto by reference.

BACKGROUND OF THE INVENTION (a) Field of the Invention

The present invention relates to a method for modification of a microchip or a lab-on-a-chip. Specifically, the present invention relates to a method for modification of microchannels of a polydimethylsiloxane (PDMS) microchip.

(b) Description of the Related Art

Recently, development of microprocessors that are capable of integrating and conducting a series of processes required for analysis including injection of an analysis sample, pretreatment, chemical reaction, detection, etc. in a miniaturized system, based on microfluidics, has been actively progressed. The system is referred to as a lab-on-a-chip or simply as a microchip. Currently, silicon, glass, quartz, etc., having electrical insulating properties and that are capable of transferring a solution under the electric fields, are widely used materials of microchips. The surface of glass has hydrophilicity, and thus channels of a glass microchip can be easily filled with an aqueous solution using the capillary phenomenon. And, it does not show surface swelling because it is chemically stable for most of solutions or gases. Further, glass can prevent small molecules in a solution from penetrating through the surface of the channels because it does not have small pores. Especially, its surface silanol group (—SiOH) imparts rapid electro-osmotic flow (EOF) and enables rapid transfer of a solution, and thus the glass microchip enables rapid analysis when conducting electrophoresis. A glass microchip is generally manufactured using photolithography. However, photolithography has defects in that, in general, it takes a long time to conduct the process and its manufacture cost is high. And, it is dangerous because microchannels are generally formed using caustics. Further, a process of joining upper and lower plates to form channels in a microchip is complicated and time consuming, and the plates are easily broken, and therefore it is difficult to widely apply photolithography for manufacture of a microchip.

Due to these limitations, a method for manufacturing a microchip rapidly and at an inexpensive cost using polymers is being actively studied.

Using soft lithography, a PDMS microchip can be manufactured by replica molding. According to the method, precursors are poured into a prepared mold and hardened at a low temperature. The method is simple and easy, and the manufacture cost is low thus enabling mass production. And, a thus-prepared PDMS microchip has good optical permeability even to UV, thus allowing detection of an analysis material by an optical method. Further, the prepared PDMS is chemically stable and does not react with other materials, it is nontoxic and thus suitable for living material, and therefore the importance thereof is increasing.

However, since the PDMS microchip has strong hydrophobicity due to repeated —Si—($CH_3$) at the surface thereof, it is difficult to fill it with an aqueous solution. It also has low and unstable EOF, and thus it is difficult to electrically transfer a solution and separate and detect a sample. Further, the structures of microchannels are easily deformed because the surface swells when an analysis sample such as a protein or a hydrophobic material is absorbed or a non-polar solvent is absorbed at its surface. For the above reasons, a PDMS microchip is difficult to apply for an organic synthesis reaction using an organic solvent that has frequently been attempted lately, as well as to a reaction using an aqueous buffer solution.

Therefore, currently, the results of many studies for facilitating electrophoresis using a PDMS microchip through the modification thereof and increasing the efficiencies of reaction and separation/analysis using a microchip by decreasing absorption of living materials thus decreasing loss of sample are being presented.

As the first example, excessive energy such as oxygen plasma, UV rays, or corona discharge is injected to silica to oxidize the surface thereof, thus obtaining a hydrophilic surface (Efimenko, K. Wallace, W. E.; Genzer, J. *Journal of Colloid and Interface Science* 2002, 254, 306). Although this method can result in high EOF, it has defects in that hydrophobic PDMS having a low molecular weight is diffused at the surface and thus hydrophilicity is maintained for a very short time.

As the second example, Ocvirk et al. disclosed a method for increasing quantity of electric charge at the surface by injecting a charged surfactant at critical micelle concentrations (CMCs) or less, thus making the hydrophobic tail thereof be absorbed at the surface of PDMS and the hydrophilic head come out of the surface (Ocvirk, G.; Munroe, M.; Tang, T.; Oleschuk, R.; Westra, K.; Harrison, D. J. *Electrophoresis* 2000, 21, 107).

According to the above two methods, a microchip is modified by injecting a solution including a compound that is active to the surface in the channels of microchip, and washing the channels with the solution, or flowing the solution together with an electrolyte. However, since these methods use electrostatic interactions, absorption and desorption reversibly occur at the surface, and thus coating stability is not good.

Accordingly, in order to solve the problem in terms of stability, many studies regarding permanent modification methods wherein a generally high energy is applied to the surface to increase surface activity and then covalent bonds are formed by chemical reactions are progressing.

Papra et al. treated a PDMS surface with oxygen plasma to oxidize the PDMS surface, and then reacted 2-[methoxy(polyethyleneoxy)propyl]trimethoxysilane and poly(ethylene glycol)di(triethoxy)silane (Si-PEG-Si) to form a covalent bond, thereby obtaining a surface that is capable of effectively preventing absorption of hydrophilic protein (Papra, A.; Bernard, A.; Juncker, D.; Larsen, N. B.; Michel, B.; Delamarche, E. *Langmuir* 2001, 17, 4090). Although this method is good in terms of coating stability compared to the above two methods, it is complicated and accordingly difficult to easily apply.

SUMMARY OF THE INVENTION

An object of the present invention is to provide a method for easily and simply modifying microchannels of a PDMS microchip so as to impart glass-like properties.

Another object of the present invention is to provide a method for modifying a defined partial area of microchannels of a PDMS microchip, so that the PDMS microchip including microchannels can be used for a stepwise organic synthetic reaction or an enzyme reaction.

A further object of the present invention is to provide a method for modifying the surface of a PDMS microchip, further including, after coating a PDMS substrate with a sol-gel solution, drying the coated surface without a crack in the coated surface.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

For a more complete understanding of the present invention, and the advantages thereof, reference is now made to the following description taken in conjunction with the accompanying drawings, in which.

DETAILED DESCRIPTION OF THE PREFERRED EMBODIMENTS

These and other objects of the invention will be more fully understood from the following description of the invention, the referenced drawings attached hereto, and the claims appended hereto.

The present invention provides a method of modification of microchannels of a PDMS microchip.

Specifically, the present invention provides a method for modification of microchannels of a PDMS microchip that includes the steps of:

a) mixing an alkoxysilane precursor of the following Chemical Formula 1, an alkyl alkoxysilane precursor of the following Chemical Formula 2, and a solvent to prepare a sol-gel solution;

b) oxidizing microchannels of a PDMS microchip; and c) coating the oxidized microchannels with the sol-gel solution prepared in step a), $$(R^1O)_4\text{—Si} \quad \text{[Chemical Formula 1]}$$

(wherein $R^1$ is $C_1$-$C_3$ alkyl), and $$(R^2)_n\text{—Si—}(OR^3)_{4-n} \quad \text{[Chemical Formula 2]}$$

(wherein $R^2$ and $R^3$ are independently a $C_1$ to $C_2$ alkyl, and n is 1 or 2).

In step a), an alkoxysilane having Chemical Formula 1, $(R^1O)_4$—Si (wherein $R^1$ is $C_1$-$C_3$ alkyl), is used as a precursor of the sol-gel solution. The alkoxysilane having carbon atoms of the above range makes a sol-gel reaction fast. If the microchannels of the PDMS microchip are coated with the alkoxysilane, hydrophilicity can largely improve. Preferably, the alkoxysilane of Chemical Formula 1 is selected from the group consisting of tetraethyl orthosilicate (TEOS), tetramethyl orthosilicate (TMOS), and tetrabutyl orthosilicate (TBOS). More preferably, tetraethyl orthosilicate (TEOS) is used.

Alkyl alkoxysilane having the Chemical Formula 2, $(R^2)_n$—Si—$(OR^3)_4$, (wherein $R^2$ and $R^3$ are independently a $C_1$ to $C_2$ alkyl, and n is 1 or 2), is used as a precursor of the sol-gel solution. If the alkyl alkoxysilane having alkyl and alkoxy groups having carbon atoms of the above ranges, cracks of the coated surface can be reduced when drying after sol-gel coating, and hydrophilicity of the finally modified surface can largely improve. Preferably, the alkyl alkoxysilane is selected from the group consisting of methyltrimethoxysilane (MTMS), ethyltriethoxysilane (ETES), methyltriethoxysilane, diethoxydiethylsilane and ethyltrimethoxysilane. More preferably, MTMS is used.

Most preferably, the precursors of the sol-gel solution are TEOS and MTMS.

In general, a sol-gel reaction consists of three reactions of hydrolysis of precursors, alcohol condensation, and water condensation. The sol-gel reactions of the precursors result in the formation of a solid phase having a 3-dimensional network structure.

Figure 1:
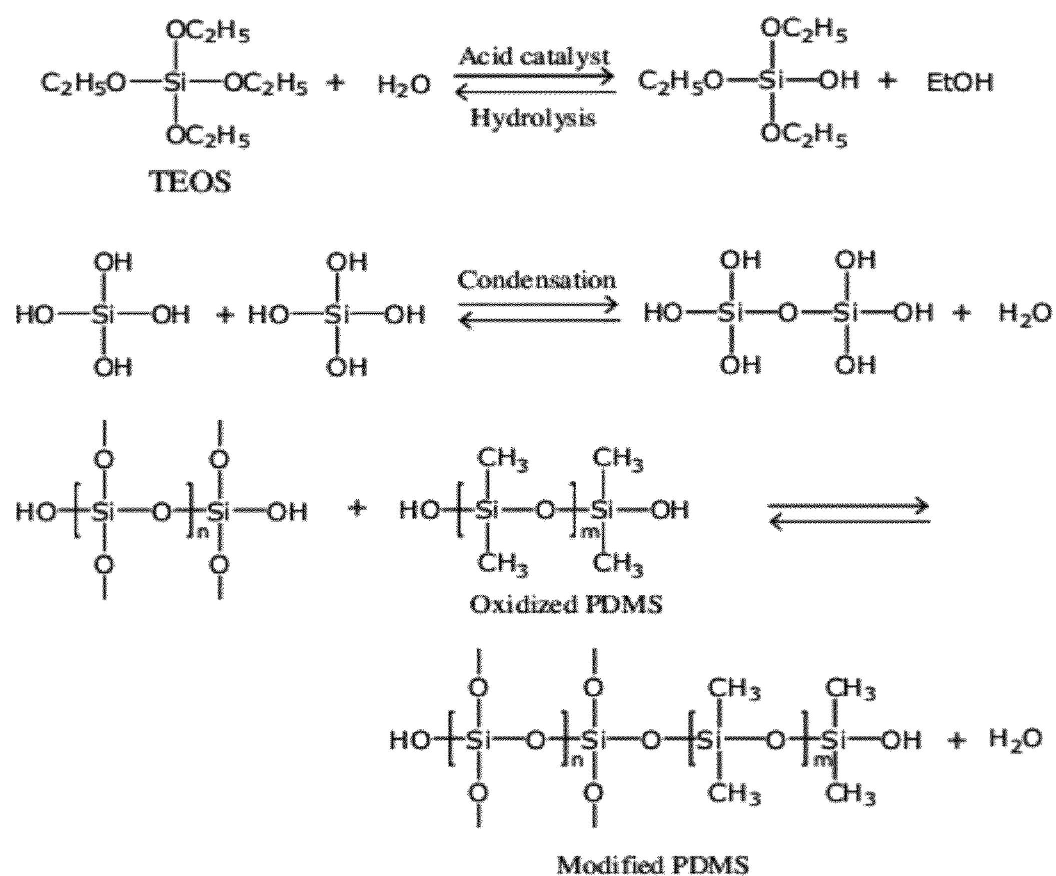
FIG. 1 shows mechanisms of a sol-gel reaction and a reaction between oxidized PDMS and a sol-gel solution.

As shown in FIG. 1, the sol-gel reaction of the sol-gel solution according to the present invention includes hydrolysis and condensation. The structure or size of sol-gel is controlled by the reaction rate of hydrolysis and condensation. The properties of the sol-gel solution coating the oxidized PDMS microchannels influence hydrophilicity of the finally modified PDMS and cracks of the coated surface when drying. Thus, in order to control the reaction rate, pH, temperature, properties, and concentration of a catalyst and a ratio of water and precursors, etc., can be controlled.

According to an embodiment of the present invention, the sol-gel solution further includes an acid catalyst selected from hydrochloric acid (HCl) and sulfuric acid ($H_2SO_4$). The rate of hydrolysis of alkoxysilane can be controlled by adding an acid catalyst. In the sol-gel solution further including an acid catalyst selected from hydrochloric acid and sulfuric acid, cross-linking is less formed because hydrolysis is faster than condensation. As a result, the sol-gel solution is flexible and can be easily injected in microchannels, and cracks of the coated surface that may occur when drying can be reduced.

In addition, unless a larger gel molecule increases viscosity and largely decreasing flexibility of the coating, the pH of the sol-gel solution can be varied, and the range of 2 to 4 is preferable. Within the acidic pH range, since hydrolysis is predominant and gel particles linearly grow, the sol-gel solution becomes flexible and cracks of the coated surface can be reduced when drying.

According to an embodiment of the present invention, alkoxysilane of Chemical Formula 1 and alkyl alkoxysilane of Chemical Formula 2 can be mixed at a volume ratio of 1 to 3:1 to prepare a sol-gel solution. If PDMS is coated with the sol-gel solution having the above volume ratio, hydrophilicity of the modified surface can largely improve, and cleavage of the coating surface due to internal pressure can be maximally reduced when drying after sol-gel coating.

According to another embodiment of the present invention, as the solvent of a sol-gel solution, an organic solvent and water can be used. Preferably, the ratio of precursors to organic solvent to water can be mixed at a volume ratio of 1:1 to 2:3~8. If a sol-gel solution is prepared with the above ratio, a sol-gel solution that is sufficiently hydrolyzed and then condensed can be obtained, and cracks of the coated surface can be reduced when drying.

As the organic solvent for the sol-gel solution, the same alcohol as produced by hydrolysis of alkoxysilane is preferably used. For example, it is selected from the group consisting of methyl alcohol, ethyl alcohol, and butyl alcohol. If the same alcohol as the hydrolysis product of alkoxysilane is used for the organic solvent, alcohol condensation that can occur together with hydrolysis can be reduced, thereby reducing cross-linking. As a result, the gel particles linearly grow and thus the sol-gel solution is flexible and can be easily injected in microchannels, and cracks of the coated surface can be reduced when drying.

In the preparation of a sol-gel solution, in order to accelerate a sol-gel reaction, a mixture is agitated or shaken simultaneously with injecting of a precursor until a reaction progresses to some extent. When the solution becomes clear, it is used for coating.

Meanwhile, the coating according to the present invention is conducted on oxidized microchannels of a PDMS substrate. The oxidation of the PDMS substrate can be conducted by plasma discharge.

Preferably, the microchannels of the PDMS microchip can be oxidized using corona discharge that is capable of oxidizing a defined partial area of microchannels. The oxidized area of the PDMS microchip can rapidly react with a sol-gel solution. If the PDMS microchip is coated with a sol-gel solution without oxidation, PDMS cannot rapidly react with the surface and flows out during rinsing, and thus the effects of surface modification are not maintained. Thus, according to the modification method of the present invention, PDMS microchannels are oxidized and then coated with a sol-gel solution.

According to another embodiment of the present invention, the oxidation can be conducted in the whole of the microchannels or in a defined partial area of the PDMS microchannels.

Only the oxidized part of the microchannels can rapidly react with a sol-gel solution. If the whole of the microchannels are oxidized and then a sol-gel solution is introduced therein, the surfaces of all microchannels are modified to be like glass. The microchip of which microchannels are surface-modified to be like glass according to the present invention can be widely applied for capillary gel electrophoresis and synthetic reaction using an organic solvent, etc., which have usually been conducted only on a glass microchip.

As described above, since only the oxidized PDMS microchannels can rapidly react with a sol-gel solution, if a defined partial area of microchannels is oxidized and a sol-gel solution is introduced therein, a sol-gel solution is coated only on the defined partial area of microchannels to produce a modified partial surface. The PDMS microchip wherein only a defined partial area of microchannels is modified can be applied for a stepwise organic synthetic reaction or an enzyme reaction.

A method for oxidizing all microchannels or only defined partial microchannels of a PDMS microchip will now be explained in detail.

A method for oxidizing all microchannels of the PDMS microchip is as follows. Pt wires are inserted into reservoirs of both ends of a microchannel, one is connected with an aluminum block, and a voltage is applied at the other using a Tesla coil to cause a corona discharge, thereby oxidizing the surface. The aluminum block functions as a ground connection, and thus if a corona discharge is caused close to a pin at the other part, the aluminum block makes a voltage difference between two pins large so that plasma can be generated only at channels of the microchip to oxidize them.

Figure 2:
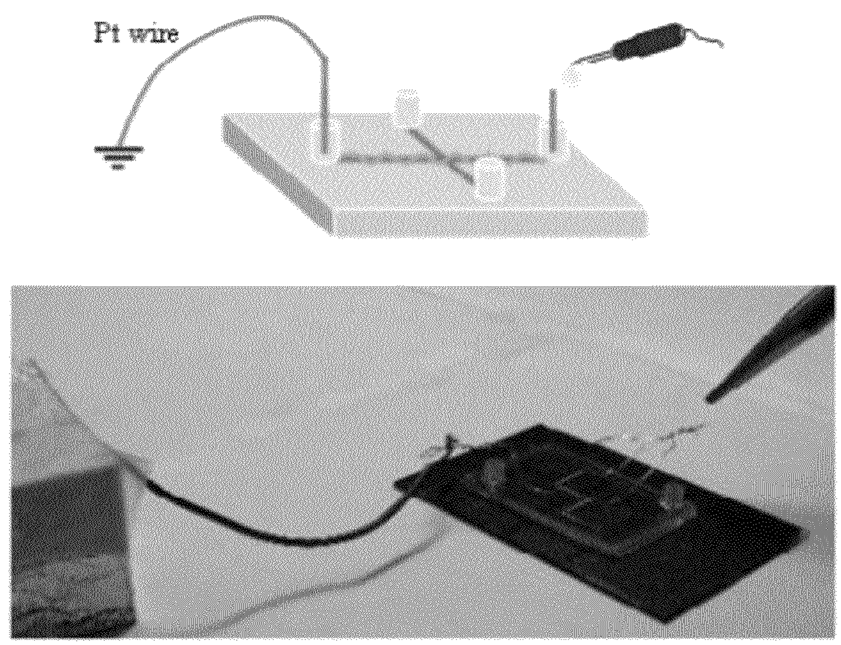
FIG. 2 shows a schematic diagram and a photo showing corona discharge of microchannels of a PDMS microchip using a Tesla coil.
Figure 3:
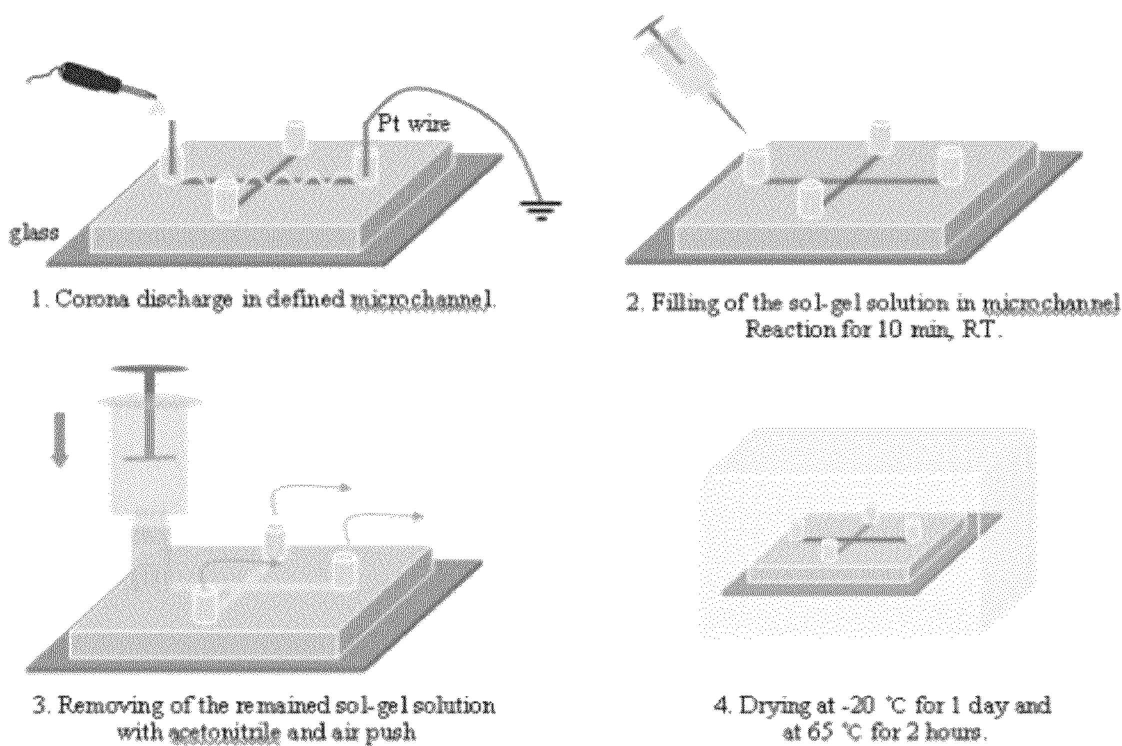
FIG. 3 is a schematic diagram showing an embodiment of processes for modifying microchannels of a PDMS microchip using a sol-gel solution.

In order to oxidize a defined partial area of the microchannels, a Pt wire can be directly inserted into a desired area of the microchannels. As shown in FIG. 2, a Pt wire is inserted into a defined area of the microchannel of a lattice shape to cause a corona discharge. In general, the PDMS microchip is plasma treated and oxidized in order to join the upper and lower plates of PDMS, and a PDMS microchip prior to passage of one week after its manufacture has silanol groups at the surface. Thus, in order to modify a defined partial area of microchannels, a PDMS microchip that is allowed to stand for at least one week after its manufacture should be used.

When oxidizing microchannels of a PDMS microchip, damage to the PDMS microchip can be reduced by sharpening a Pt wire and perpendicularly inserting it into a desired area.

Meanwhile, corona discharge time should be within a range that does not burn PDMS to make it opaque, and discharge time can be varied according to the size of channels so as to maintain reproducibility of coating. Preferably, the corona discharge time is from 1 to 10 seconds.

In step c), the coating is conducted by injecting a sol-gel solution in the oxidized PDMS microchannels. The oxidized PDMS microchannels are filled with a sol-gel solution and are allowed to react at room temperature. Before the sol-gel solution is hardened, unreacted solution is rinsed and removed using an organic solvent. Reaction time for a sol-gel solution filled in the surface of microchannels is determined to be as long as possible, unless the sol-gel solution is hardened in the channels. When modifying a defined partial area of microchannels, the reaction time is controlled so that an area not to be oxidized with corona-discharge may not be coated. Preferably, a sol-gel solution is left to stand for 5 to 10 minutes and then rinsed.

After coating, the coated PDMS substrate can be rinsed and dried.

In the rinsing step, an organic solvent is flowed to microchannels and then the unreacted sol-gel solution is dissolved in the organic solvent and rinsed. An organic solvent that is not involved in the sol-gel reaction is preferably used in the rinsing step. In case an alcohol is used as the organic solvent in the rinsing step, a reverse reaction of hydrolysis (esterification) and a reverse reaction of alcohol condensation (depolymerization) may occur to make the coating surface opaque, and thus the rinsing step should be carefully conducted. Preferably, an organic solvent used for rinsing can be selected from the group consisting of hexane, xylene, toluene, and acetonitrile.

After rinsing with an organic solvent to remove remaining sol-gel solution, drying may be conducted in order to remove the solvent of the sol-gel solution such as water or alcohol remaining on the surface. The drying step should be conducted slowly in order to prevent cracks of the coated surface due to internal pressure that is generated with the solvent removal, and to completely remove the solvent, which can guarantee long use of the microchip under the same conditions. If the drying is conducted at room temperature for 12 hours or more, the cracks of the coated surface can be reduced and the solvent can be completely removed. Preferably, the drying is conducted at 4° C. to 20° C. for 12 to 48 hours. More preferably, after drying at room temperature, additional drying may be conducted at 60° C. to 80° C. for 1 to 5 hours. The additional drying under high temperature conditions can remove the solvent completely. After drying at room temperature and/or additional drying at high temperature, a PDMS microchip of which the surface of microchannels is modified so as to have glass-like properties can be obtained.

In order to confirm the surface properties of a PDMS microchip modified by using a sol-gel solution, a hydrophilicity test, a non-polar substance absorption test, and an organic solvent resistance test were conducted.

In order to test hydrophilicity, a contact angle was measured. And, in order to test absorptiveness of a non-polar substance, a fluorescent non-polar substance was filled in the microchannel and the degree of non-polar substance spread with the passage of time was identified by fluorescence detection. In order to test organic solvent resistance, the microchannel was filled with an organic solvent and cut to identify a change of a cross-section by a CCD camera.

In order to confirm the utility of the modified PDMS microchip according to the present invention, capillary gel electrophoresis (CGE) that could not be easily applied to an unmodified PDMS microchip was tested.

In order to effectively conduct CGE, a polyacrylamide gel was used as a stationary phase (Brahmasandra, S, N.; Ugaz, V. M.; Burke, D. T.; Mastrangelo C. H.; Burns, M. A. Electrophoresis 2001, 22, 300). For introduction into a microchip, a polyacrylamide gel should be able to be fixed to a specific part to be separated. Then, a DNA separation process and a pretreatment process such as sample injection can be easily included in a microchip so as to enable integrated analysis. For this, the gel was fixed to a desired part of microchannels through masking using acrylamide of which cross-linking is induced by UV. Using a microchip filled with a gel, a voltage was applied to each reservoir to conduct gel electrophoresis of DNA and the signal of separated DNA was obtained using laser-induced fluorescence.

The present invention is further explained in more detail with reference to the following examples. These examples, however, should not be interpreted as limiting the scope of the present invention in any manner.

EXAMPLE 1

Preparation of Sol-Gel Solution

Tetraethyl orthosilicate (TEOS) and methyltrimethoxysilane (MTMS) were used as precursors, ethanol was used as a solvent, and hydrochloric acid was used as an acid catalyst. 0.01M hydrochloric acid was prepared, and hydrolysis of the sol-gel process was conducted using water in the hydrochloric acid solution. The volume ratio of precursors, ethanol, and water was 1:1:4, and the volume ratio of precursors TEOS and MTMS was 2.5:1. 734 μl of TEOS, 187.5 μl of MTMS, 268 μl of ethanol, and 331 μl of hydrochloric acid were added to a microtube in order, and agitated at 1400 rpm for 5 hours.

EXAMPLE 2

Modification of PDMS Microchip 2.1. Modification of the Whole of Microchannels of a PDMS Microchip 2.1.1 Oxidation of the Whole of Microchannels A PDMS microchip was sufficiently washed with methanol, and then dried in a 65° C. oven for 30 minutes or more to completely remove the methanol. Pt wires were inserted into reservoirs of both ends of a microchannel to be oxidized, and one was connected to an aluminum block. Corona discharge was conducted for 10 seconds, for a straight channel of 100 μm in width, 100 μm in depth, and 3 cm in length. Corona discharge time was varied in proportion to width, depth, and length of microchannel.

Figure 4A:
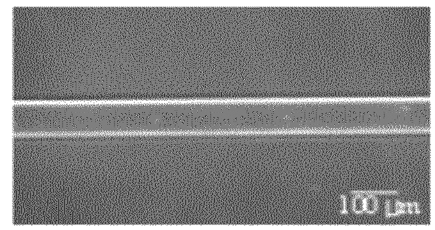
FIG. 4*a* is a charge coupled device (CCD) image of microchannels of an unmodified PDMS microchip.
Figure 4B:
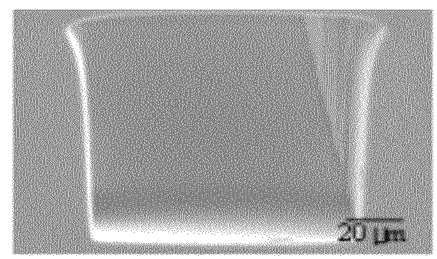
FIGS. 4*b* and 4*c* are SEM images thereof.
Figure 4C:
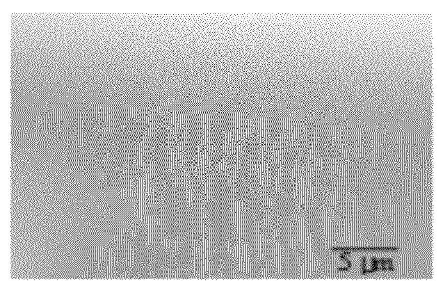
Figure 5A:
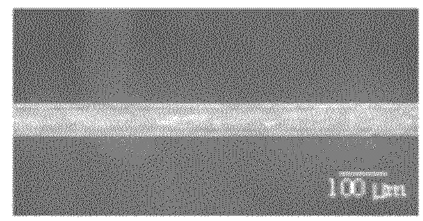
FIG. 5*a* is a CCD image of microchannels of a PDMS microchip that is modified according to an embodiment of the present invention.
Figure 5B:
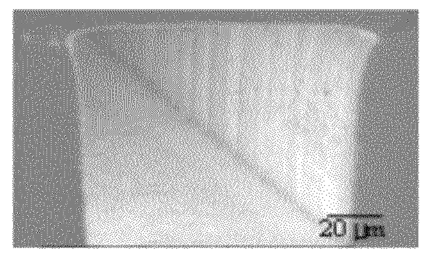
FIGS. 5*b* and 5*c* are SEM images thereof.
Figure 5C:
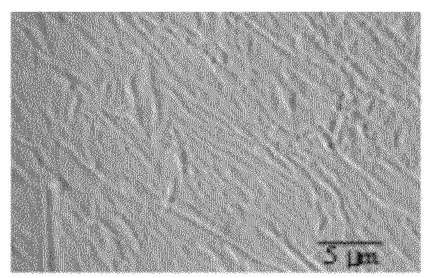

2.1.2 Coating of the Oxidized PDMS Microchannels with Sol-Gel Solution, Rinsing, and Drying PDMS microchannels were filled with a sol-gel solution, and the sol-gel solution was injected in each reservoir so that the microchannels may not get dry. After standing at room temperature for 10 minutes so that the sol-gel could react with the PDMS surface, the sol-gel solution was removed from each reservoir, and then acetonitrile was flowed to the channels to rinse unreacted sol-gel solution. In order to completely remove acetonitrile in the microchannels, tissue was inserted in one reservoir and pushed from the other reservoir with a syringe. Approximately 0.2 ml of acetonitrile was used for a straight microchip of 3 cm in length. Drying was conducted at 4° C. for 12 hours, and then in a 65° C. oven for 2 hours or more to completely remove the solvent. FIG. 5 shows a CCD camera image and an SEM image of modified PDMS microchannels. Comparing the images of FIG. 5 with the images of unmodified PDMS microchannels shown in FIG. 4, it is confirmed that cracks of the coated surface did not occur in the modified PDMS microchannels and the microchannels were uniformly modified.

2.2 Modification of a Defined Partial Area of Microchannels of PDMS Microchip 2.2.1. Oxidation of a Defined Area of Microchannels In order to modify the surface of defined PDMS microchannels, a microchip that was allowed to stand for one week or more at room temperature after its manufacture was used. For modification of a defined partial area of microchannels, a microchip with channels of a lattice shape of 1 cm intervals was used. In order to oxidize a desired area of a channel network, a sharpened Pt wire was directly inserted in the PDMS microchannel, one end was connected to an aluminum block, and corona discharge was conducted. FIG. 2 shows corona discharge of a defined partial area of channels.

Figure 6:
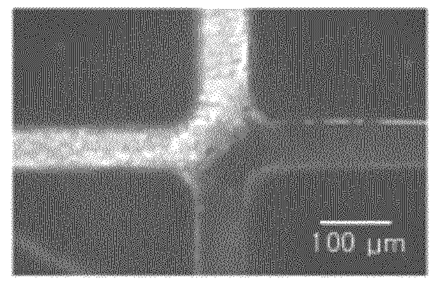
FIG. 6 is a CCD image of a PDMS microchip wherein defined microchannels are modified according to an embodiment of the present invention.
Figure 7:
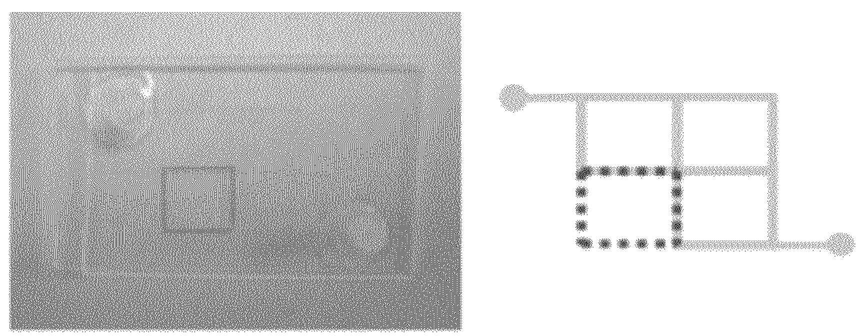
FIG. 7 shows photos of a microchip wherein a defined area of PDMS microchannels of a lattice shape is modified and the modified area is filled with an ink.
Figure 7:
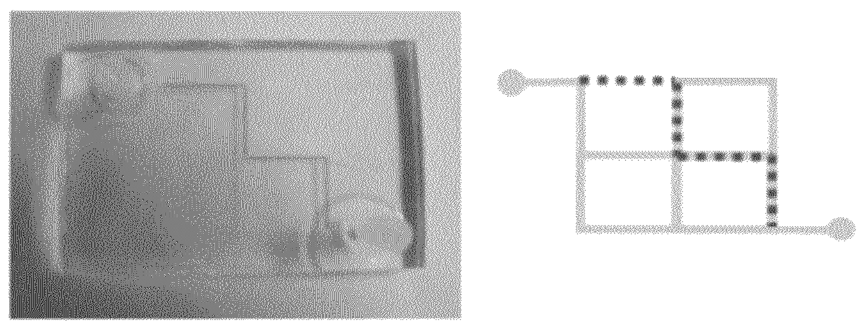

2.2.2. Coating PDMS Microchip of which Defined Partial Area of Microchannels are Oxidized with Sol-Gel Solution, Rinsing, and Drying Coating of PDMS microchannels, rinsing, and drying were conducted in the same manner as explained in the section 2.1.2. FIG. 6 shows a CCD image of PDMS microchannels of which a defined area was modified. Comparing FIG. 6 with the CCD image of unmodified PDMS microchannels in FIG. 4, it is confirmed that only a desired partial area of microchannels can be modified. FIG. 7 shows the results of filling ink only in the hydrophilically modified microchannels.

EXAMPLE 3

Figure 8:
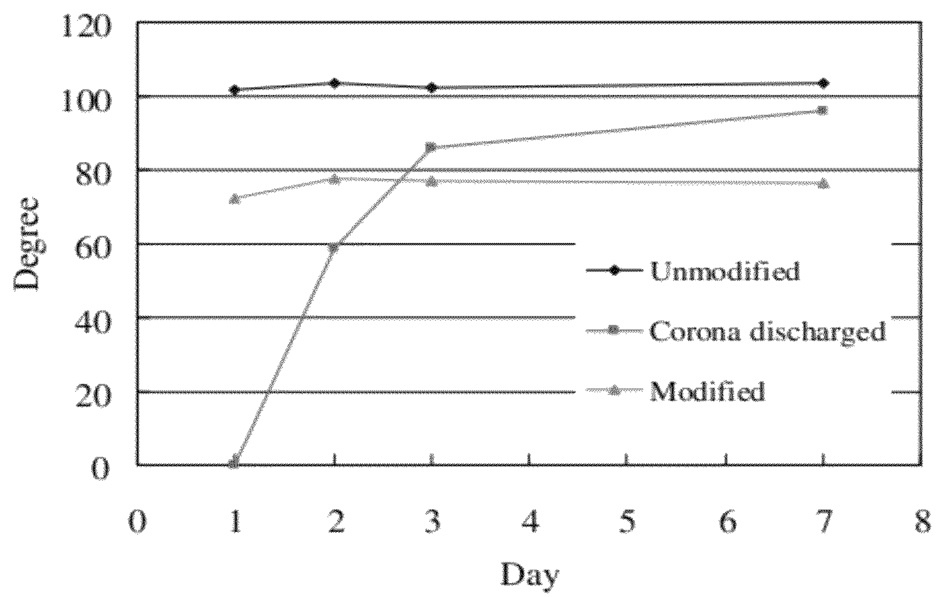
FIG. 8 is a graph showing change in contact angles of unmodified PDMS, modified PDMS according to an example of the method of the present invention, and PDMS of which the surface is oxidized by corona discharge according to elapse of time.

Analysis of Properties of PDMS Microchip Modified with Sol-Gel 3.1. Measurement of Contact Angle In order to measure hydrophilicity, contact angles of the surfaces of PDMS modified with a sol-gel solution and unmodified PDMS were measured. The contact angle was measured by a drop shape analysis system (DSA-10 KRÜSS GmbH, Hamburg, Germany), which measures the angle between tangents of a base line of a liquid drop on a solid surface and a boundary line of the drop. A syringe filled with water was fixed perpendicularly to the PDMS surface, and water was slowly dripped from a 3 mm-4 mm height. After 30 seconds, an angle was measured using drop shape analysis software. The more hydrophilic the surface is, the less the contact angle is because the water drop contacts the surface more broadly. Measurement was repeated three or four times, and the average value was calculated. FIG. 8 shows the results of measuring contact angle, and it shows that in a case of only corona-discharge, the surface rapidly recovers hydrophobicity, while in a case of further coating with a sol-gel solution, the surface maintains hydrophilicity of the surface for one week or more. The contact angles of glass and unmodified PDMS were respectively 37° and 103°, and the contact angle of the PDMS that is surface-modified with a sol-gel solution was approximately 76°, which is a middle value between PDMS and glass. Thus, it is confirmed that the surface of PDMS becomes hydrophilic by surface modification using a sol-gel solution.

3.2. Measurement of EOF Mobility

Figure 9:
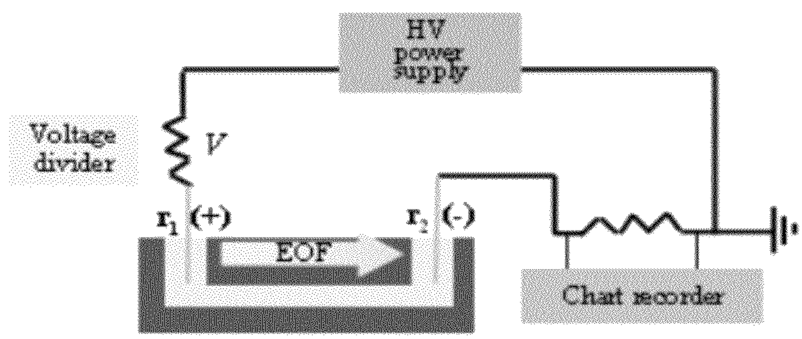
FIG. 9 is a schematic diagram of an apparatus for measuring EOF mobility.

EOF mobility of PDMS microchannels was measured by current monitoring (Huang, X.; Gordon, M. J.; Zare, R. N. Analytical Chemistry 1988, 60, 1837). An unmodified PDMS microchip with straight channels of 200 μm in width, 100 μm in depth, and 3 cm in length, and a PDMS microchip that was modified with a sol-gel solution were prepared. Both reservoirs including channels were filled with 100% boric acid buffer to the same water level without bubbles. 25 mM of boric acid buffer is assumed to be 100%. As shown in FIG. 9, using an EOF measuring apparatus manufactured in the laboratory, Pt wires were inserted in both reservoirs of a microchannel and a voltage of 400V was applied thereto. After confirming that the current value in the chart recorder was stabilized, the buffer was removed at reservoir 1 (left), and the reservoir 1 was filled with 50% boric acid buffer to the same water level as the reservoir 2. Buffer of lower concentration also flowed along the microchannel by EOF generated by applied a high voltage, and the generated current decreased. EOF mobility is calculated by the following Equation 1 (wherein L is the length along which buffer solution moves, i.e., the length of channel, Δt is time for which buffer solution of a lower concentration passes the microchannel, which is measured by calculating the time from the point when current in the chart recorder begins to change to the point when the current is stabilized, and V is applied voltage).

$$\mu_{EOF} = \frac{v_{EOF}}{E} = \frac{L}{\Delta t}\frac{L}{V} = \frac{L^2}{\Delta t V} \quad \text{[Equation 1]}$$

Figure 10A:
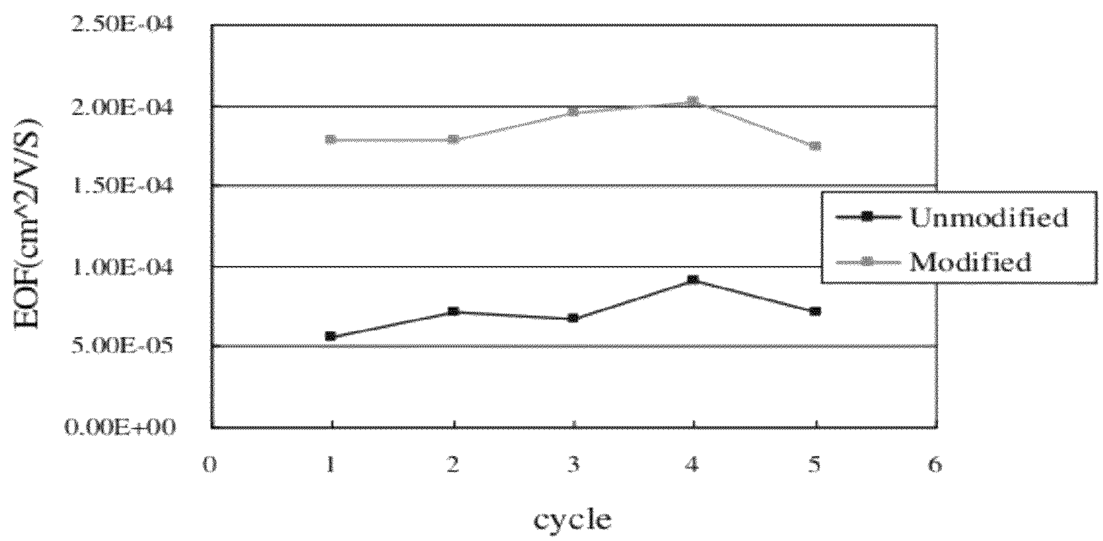
FIG. 10*a* is a graph showing the results of measuring stabilities of EOF in unmodified PDMS microchannels and in modified PDMS microchannels.
Figure 10B:
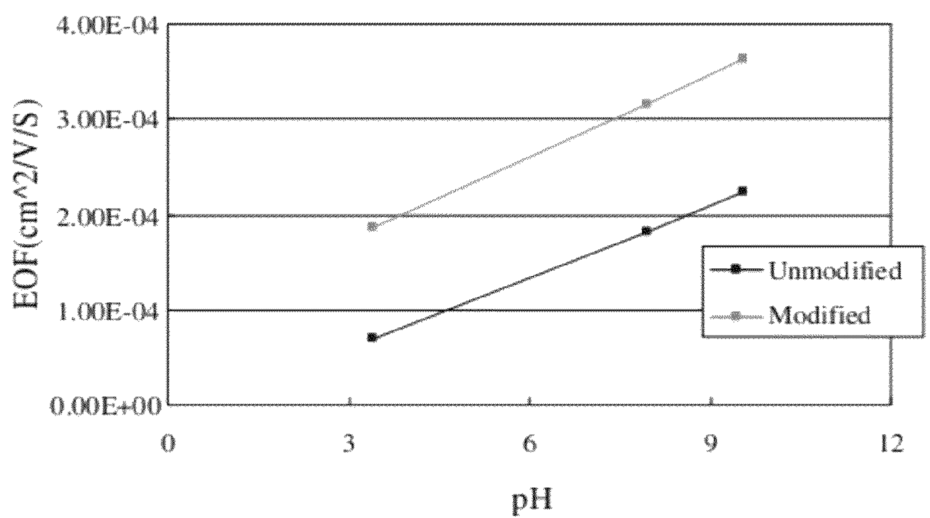
FIG. 10*b* is a graph showing the results of measuring EOF changes according to pH change in unmodified PDMS microchannels and in modified PDMS microchannels.

EOF was repeatedly measured 5 times at buffer pH of 3 to test stability, and EOF change according to pH change was tested, of which results are shown in FIG. 10. Unmodified PDMS shows low EOF mobility due to a surface methyl group, while PDMS modified with a sol-gel solution shows a much increased surface potential (ξ potential) because surface silanol groups increase at the surface and the amount of Si—O$^-$ ionization also significantly increases. Although there was little difference between the stabilities of an unmodified PDMS microchannel and a modified PDMS microchannel because both showed a standard deviation of $1.2\times10^{-5}$, EOF mobility increased 2.6 times after surface modification. And, the modified PDMS microchannel showed about 2 times higher mobility than the unmodified PDMS microchannel at the broad range of pH 3, 8, and 10.

3.3. Measurement of Absorptiveness of Non-Polar Substance

In order to examine the degree of absorption of a neutral substance due to hydrophobicity and porosity of PDMS, experiments were conducted using non-polar fluorescent BODIPY (4,4-difluoro-1,3,5,7-tetramethyl-4-bora-3a,4a-diaza-s-indacene-8-propionic acid). In order to easily understand the degree of absorption, a PDMS microchip with cross-shaped channels with a 200 μm width and a 100 μm depth was prepared. And, the microchannels were filled with 30 μM of BODIPY solution dissolved in 1×TBE buffer of pH 8, and the degree of spread of BODIPY toward PDMS according to elapse of time was examined using a laser-induced fluorescence system.

Figure 11A:
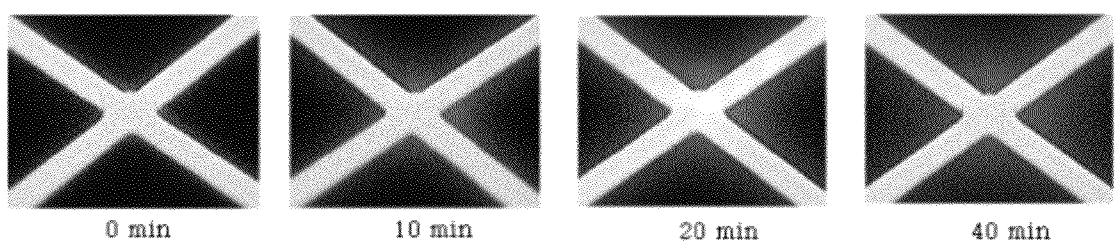
FIG. 11*a* is CCD images showing absorptivity of a non-polar substance according to elapse of time in unmodified PDMS microchannels.
Figure 11B:
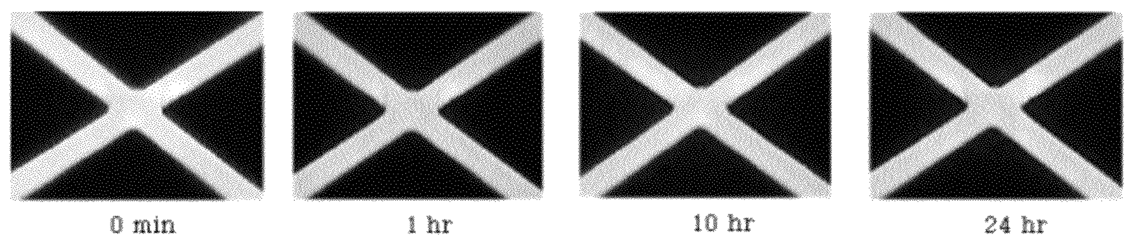
FIG. 11*b* is CCD images showing absorptivity of a non-polar substance according to elapse of time in modified PDMS microchannels.

FIG. 11 is the results of fluorescence detection, which shows that in the case of unmodified PDMS, the image even after 10 minutes has very high fluorescence intensity at PDMS, confirming that a great quantity of BODIPY was absorbed in the unmodified PDMS. In the case of modified PDMS, the amount of absorbed BODIPY is very small even after 24 hours, and thus, although slight fluorescence is detected, fluorescence intensity is very low compared to the unmodified DPMS microchip after ten minutes. However, it was examined that after 48 hours or more from filling BODIPY, although not lighting up from the lattice point as seen in the unmodified PDMS microchip, general fluorescence intensity increases. Thus, it is confirmed that absorption of a non-polar substance into microchip can be effectively prevented by modifying a PDMS microchip with a sol-gel solution.

3.4. Measurement of Absorptiveness of Organic Solvent

Figure 12:
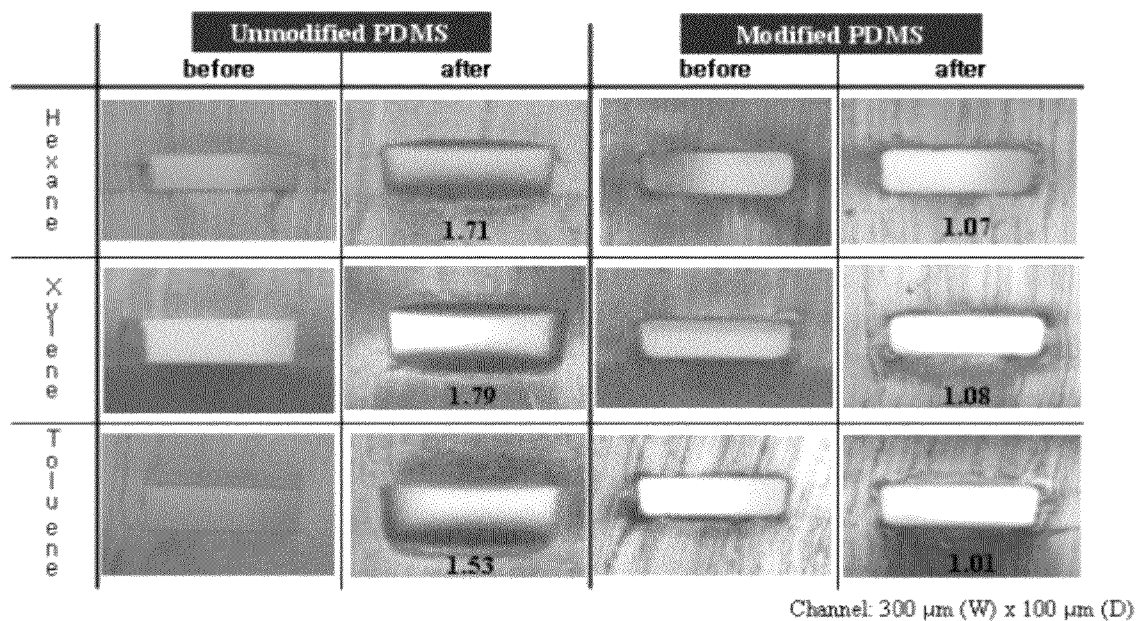
FIG. 12 compares the degrees of swelling of unmodified PDMS microchannels and modified PDMS microchannels for an organic solvent.

Organic solvent resistance was measured using a property of PDMS swelling when absorbing an organic solvent. An unmodified PDMS microchip with channels of 300 μm in width and 100 μm in depth, and a PDMS microchip that was modified with a sol-gel solution were prepared. After flowing an organic solvent into the microchannels for 10 minutes, the microchannels were cut to a 5 mm width to obtain CCD images. As the organic solvent, xylene, hexane, and toluene were used. The size of microchannels obtained by a CCD camera was calculated by converting into pixel numbers using an image analysis function of Image J 1.37 v. On the basis of calculated pixel number, the degree of swelling of PDMS microchannels was measured, of which results are shown in FIG. 12. It shows that the swelling ratios of unmodified PDMS microchannels are calculated as 1.71, 1.79, and 1.53 respectively for hexane, xylene, and toluene, while the swelling ratios of modified PDMS microchannels are 1.07, 1.08, and 1.01 for the three organic solvents, confirming that little swelling occurred.

EXAMPLE 4

Gel Electrophoresis Experiment Using Modified PDMS Microchip Prepared in Example 2

4.1. Preparation of PDMS Microchip Surface-Modified with Sol-Gel

Capillary gel electrophoresis that could not be easily applied in an unmodified PDMS microchip was attempted in the surface-modified PDMS microchip according to the present invention. For separation of DNA using CGE, a modified PDMS microchip with cross-shaped channels of 200 μm in width and 100 μm in depth was prepared according to the method of section 2.1 of EXAMPLE 2.

4.2. Injection of Acrylamide in Microchannels for Separation and Fixation

DNA separation is conducted in the area below cross-shaped channels of a PDMS microchip. This area was polymerized using acrylamide of which polymerization is induced by light, and then polyacrylamide gel was fixed in the channels in the following method. As the acrylamide monomer, Reprogel™ 377 (Amersham Biosciences, NJ, USA) that is on the market was used. The Reprogel™ 377 solution consists of A and B, A being a solution including acrylamide and bisacrylamide solutions, and B being a solution including a denaturing agent and a UV initiator. The A and B solutions were sufficiently mixed at a volume ratio of 1:1, bubbles were completely removed in a vacuum chamber, and then the solution was injected in the PDMS microchannels without generating bubbles. In order to induce polymerization only in desired area, channels excluding separation channels were subjected to masking.

4.3. Conducting Polymerization

Masking was conducted using glass deposited with chromium while identifying the location by CCD camera, and the channels were exposed to a Xe/Hg lamp (Oriel Corp., Stratford, Conn., USA) to conduct polymerization by light. Then, 6% (w/v) polyacrylamide gel including a 1×TBE (Tris-Borate-EDTA) buffer solution was obtained. The part of a channel where gel does not form was sufficiently washed with the 1×TBE buffer solution, and the channel was filled with the buffer solution so that gel may not get dry until conducting CGE.

4.4. Preparation of Buffer Solution and DNA Sample

As the buffer solution for electrophoresis, 1×TBE buffer solution was used. As a DNA sample for separation, a DNA ladder including 5 DNAs of 50, 150, 300, 500, 750, and 1000 bp in which YOYO-1 is intercalated for detection by laser-induced fluorescence was used. The DNA sample was prepared by mixing 30 ml of 30-40 ng/ml DNA ladder and 1 ml of intercalator YOYO-1 and then adding 50 ml of 5×TBE buffer solution of pH 8. The YOYO-1 intercalated DNA sample solution was allowed to stand in a dark room for about 30 minutes so as to sufficiently react.

4.5. Injection of DNA Sample and Analysis

Figure 13A:
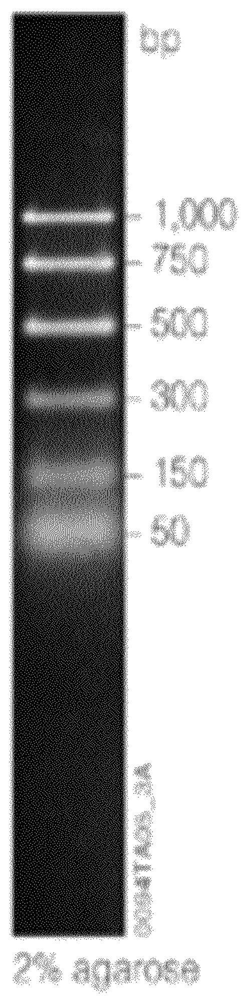
FIG. 13*a* shows the result of gel electrophoresis of ladder DNA in an unmodified PDMS microchip.
Figure 13B:
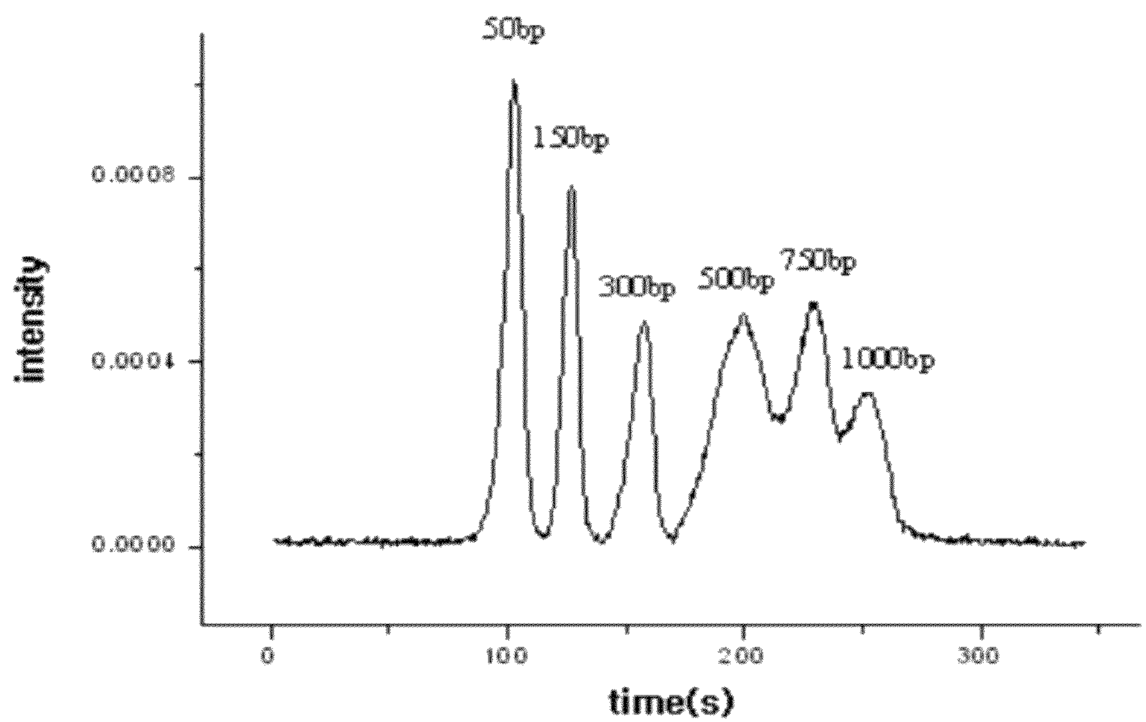
FIG. 13*b* shows the results of capillary gel electrophoresis (CGE) of ladder DNA in a modified PDMS microchip.

Pt wires were inserted into each reservoir of a microchip, and an electric field of 100 V/cm was applied for 30 minutes to remove non-solidified acrylamide remaining in the separation channel and stabilize current in the channel. A voltage of 340 V/cm was applied for 1 second for injection of the DNA sample, and a voltage of 100 V/cm was applied for separation. An argon ion laser was transmitted to a point approximately 1.5 cm apart from the DNA injection point, and the produced fluorescence signal was concentrated using an object lens. In order to obtain only the signals of YOYO-1 that reacted with DNA, noise was removed by diffusion, etc., using a filter and a pin hole, and then fluorescence signals were continuously received with a PMT (photo multiplier module) to obtain a DNA separation graph. FIG. 13*a* shows the results of separation of the DNA ladder by general slab gel electrophoresis in the unmodified PDMS microchip, and FIG. 13*b* shows the result of capillary gel electrophoresis in the modified PDMS microchip. According to the graph of FIG. 13*b*, all of 5 peaks can be observed, and good separations at 50, 150, and 300 bps show that high density gel did not form because UV exposure time was very short at about 5 minutes. Further, all of the 5 peaks can be separated within 5 minutes, indicating that the long duration of the existing electrophoresis can be overcome.

What is claimed is:

1. A method for modification of microchannels of a polydimethylsiloxane (PDMS) microchip, which comprises the steps of:

a) preparing a sol-gel solution consisting of an alkoxysilane precursor of the following Chemical Formula 1, an alkyl alkoxysilane precursor of the following Chemical Formula 2, a solvent, and an acid catalyst selected from the group consisting of hydrochloric acid and sulfuric acid;

b) oxidizing microchannels of the PDMS microchip; and c) coating the oxidized microchannels with the sol-gel solution prepared in step a), $(R^1O)_4$—Si [Chemical Formula 1]

(wherein $R^1$ is $C_1$-$C_3$ alkyl), and $(R^2)_n$—Si—$(OR^3)_{4-n}$ [Chemical Formula 2]

(wherein $R^2$ and $R^3$ are independently a $C_1$ to $C_2$ alkyl, and n is 1 or 2), wherein the modified PDMS microchip is hydrophilic.

2. The method according to claim 1, further comprising the steps of rinsing and drying the coated PDMS microchip, after the step c).

3. The method according to claim 1, wherein the alkoxysilane is selected from the group consisting of tetraethyl orthosilicate (TEOS), tetramethyl orthosilicate (TMOS) and tetrabutyl orthosilicate.

4. The method according to claim 1, wherein the alkyl alkoxysilane is selected from the group consisting of methyltrimethoxysilane (MTMS), ethyltriethoxysilane (ETES), diethoxydiethylsilane, and ethyltrimethoxysilane.

5. The method according to claim 1, wherein the sol-gel solution has pH of 2 to 4.

6. The method according to claim 1, wherein the alkoxysilane and the alkyl alkoxysilane are mixed at a volume ratio of 1 to 3:1.

7. The method according to claim 1, wherein the solvent is a mixture of an organic solvent and water, and the precursors, the organic solvent, and water are mixed at a volume ration of 1:1 to 2:3 to 8.

8. The method according to claim 1, wherein, the oxidation in the step b) is conducted by plasma discharge.

9. The method according to claim 8, wherein the plasma discharge is corona discharge.

10. The method according to claim 9, wherein the corona discharge is conducted for 1 to 10 seconds.

11. The method according to claim 3, wherein the oxidation in the step b) is conducted in at least a part of the microchannels of a PDMS microchip.

12. The method according to claim 2, wherein the rinsing is conducted with an organic solvent selected from the group consisting of hexane, xylene, toluene, and acetonitrile.

13. The method according to claim 2, wherein the drying is conducted at a temperature of 4° C. to 20° C. for 12 to 48 hours.

14. The method according to claim 13, further comprising the step of drying at 60° C. to 80° C. for 1 to 5 hours.

* * * * *